United States Patent [19]
Jaehrling et al.

[11] Patent Number: 5,183,472
[45] Date of Patent: Feb. 2, 1993

[54] ARRANGEMENT FOR TRANSCUTANEOUS FILLING OR REPLENISHMENT OF LIQUID MEDICATIONS IN AN IMPLANTABLE MEDICATION DOSING DEVICE

[75] Inventors: Peter Jaehrling, Puschendorf; Eugen Schweikert, Bubenreuth, both of Fed. Rep. of Germany

[73] Assignee: Siemens Aktiengesellschaft, Munich, Fed. Rep. of Germany

[21] Appl. No.: 629,620

[22] Filed: Dec. 18, 1990

[30] Foreign Application Priority Data

Dec. 21, 1989 [EP] European Pat. Off. ........ 89123701.8

[51] Int. Cl.⁵ ............................................. A61M 25/00
[52] U.S. Cl. ..................................... 604/284; 604/905; 604/252; 604/256; 128/DIG. 12
[58] Field of Search ................. 604/256, 29, 252, 284, 604/30–35, 283, 86–88; 128/DIG. 12

[56] References Cited

U.S. PATENT DOCUMENTS

| | | | |
|---|---|---|---|
| 4,116,646 | 9/1978 | Edwards | 604/252 |
| 4,306,976 | 12/1981 | Bazzato | 604/29 |
| 4,551,130 | 11/1985 | Herbert et al. | 604/256 |
| 4,618,343 | 10/1986 | Polaschegg | 604/29 |
| 4,936,831 | 6/1990 | Jaehrling et al. | 128/DIG. 12 |
| 4,936,832 | 6/1990 | Vaillancourt | 128/DIG. 12 |
| 5,053,003 | 10/1991 | Dadson et al. | 604/284 |

Primary Examiner—C. Fred Rosenbaum
Assistant Examiner—Chalin Smith
Attorney, Agent, or Firm—Hill, Steadman & Simpson

[57] ABSTRACT

An arrangement suitable for transcutaneous filling or replenishment of liquid medications in a medication reservoir of an implantable medical dosing device, the implantable device being of the type having a pierceable septum in fluid communication with the reservoir, has a cannula adapted at one end for piercing the septum from the exterior, and having a flexible conduit connected to an opposite end. The flexible conduit is terminated by a further pierceable septum. A syringe containing the medication can be inserted through the further septum for transferring the medication from the syringe through the flexible conduit and cannula to the medication reservoir.

5 Claims, 1 Drawing Sheet

ARRANGEMENT FOR TRANSCUTANEOUS FILLING OR REPLENISHMENT OF LIQUID MEDICATIONS IN AN IMPLANTABLE MEDICATION DOSING DEVICE

BACKGROUND OF THE INVENTION

1. Field of the Invention

The present invention is directed to an apparatus for transcutaneous filling or replenishment of liquid medications in an implantable medication dosing device of the type having a medication reservoir in fluid communication with a pierceable septum.

2. Description of the Prior Art

Implantable medication dosing devices are known in the art for dispensing liquid medication such as insulin, cytostatics or pain relievers on a time controlled basis. Such known devices include a medication reservoir which must be refilled at specific chronological intervals, which are dependent on the medication requirements of the patient. Such refilling typically takes place transcutaneously by means of an injection syringe having a cannula which pierces the skin as well as piercing a septum which is in fluid communication with the medication reservoir, the septum normally sealing the reservoir to prevent leakage of the medication therefrom. Such a structure is described in German OS 36 05 664.

SUMMARY OF THE INVENTION

It is an object of the present invention to provide an arrangement which enables a reliable refilling of the medication reservoir of implantable dosing devices of the type described above, whereby the risk of breaking, bending or slippage of the cannula from the paracentesis location is minimized.

It is further object of the present invention to provide such an arrangement wherein the risk of incorrect medication injections is minimized as well.

The above objects are achieved in accordance with the principles of the present invention in an apparatus for filling or replenishing liquid medication in the medication reservoir of an implantable dosing device wherein the cannula has a first end which is adapted to pierce the septum of the reservoir, and has an opposite end connected to a flexible conduit, the conduit being terminated by a further pierceable septum. The first end of the cannula pierces the skin and the septum of the reservoir, thereby permitting medication residues in the reservoir to be drawn out by suction by means of a syringe which punctures the further pierceable septum which terminates the conduit. Fresh medication can then be supplied to the reservoir with a further syringe, also puncturing the pierceable septum which terminates the conduit.

For extraction and refilling of medication, the skin of the patient and the septum of the medication dosing device, are pierced only by a single time, and the mechanical stress on the cannula is reduced by the flexible conduit connection between the paracentesis location of the cannula and the extraction or refilling syringe. Bending, breaking or slippage of the cannula, and the associated risk of injury to the patient or an improper injection, are thereby prevented.

When the medication residue is extracted, a negative pressure (i.e., a pressure less than atmospheric pressure) arises in the reservoir, which produces a suction effect in the subsequent replenishment of fresh medication. This suction effect facilitates the refilling of the reservoir. In the event of a leak, the negative pressure also prevents the medication from emerging from the implanted device in the refilling process and leading to an incorrect injection which could be life-threatening under certain circumstances. To maintain the negative pressure in the refilling arrangement, the conduit and the pierceable septum at the end thereof consist of material having sufficient mechanical strength so as to withstand compression in the presence of negative pressures of the magnitude which can be expected to be created in the reservoir.

In a further embodiment of the invention, a filter is disposed in the path of the conduit between the further pierceable septum and the cannula, and a further flexible conduit, also terminated by another pierceable septum, is in fluid communication with the cannula in the region between the cannula and the filter arrangement in the first flexible conduit. Extraction of medication residue takes place via the further conduit, and the refilling is undertaken via the first conduit having the filter therein, so that particles which may possible be contained in the medication to be introduced are prevented from proceeding into the medication dosing device.

In a further embodiment of the invention, an effective retention of particles contained in the refilling medication, as well as particles formed in the filter itself due to the separation of fibers therein, is achieved by constructing the filter as a membrane filter consisting of at least two membranes. A first membrane, disposed closer to the pierceable septum which terminates the flexible conduit, consists of a polypropylene fiber fleece oriented opposite the flow direction of the medication coming from the pierceable septum. A second membrane consists of a braided weave. Given an area of approximately 1 $cm^2$, a medication flow of 50–120 ml per minute, and a maximum pressure differential of 100 mbar, the first membrane preferably has a retention rate of greater than or equal to 5 $\mu m$, and the second membrane has pore size of 25 $\mu m$, the second membrane having no pores which extend straight through the second membrane.

DESCRIPTION OF THE PREFERRED EMBODIMENTS

Figure 1:
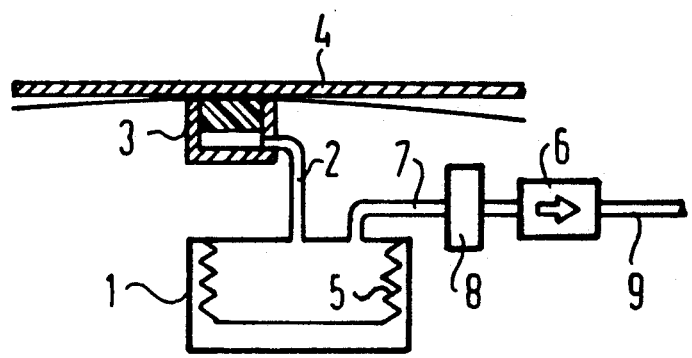
FIG. 1 is a schematic diagram of an implanted medical dosing device of the type known in the art.

A basic structure for a known implantable medication dosing device is shown in simplified form in FIG. 1. The device includes a medication reservoir 1 connected via a conduit 2 to a refilling septum 3. The refilling septum 3 is disposed immediately beneath and adjacent the skin 4 of a patient. Liquid medication such as, for example, insulin can be supplied to a membrane bellows 5 within the reservoir 1 by means of a cannula inserted through the refilling septum 3. A medication dosing pump 6 draws the stored medication in dosed portions from the reservoir 1 via a conduit 7, which may possibly have a filter 8 therein. The dosed medication is conducted to a catheter 9 which conveys the medication to a suitable location in the body of the patient in whom the device is implanted.

Figure 2:
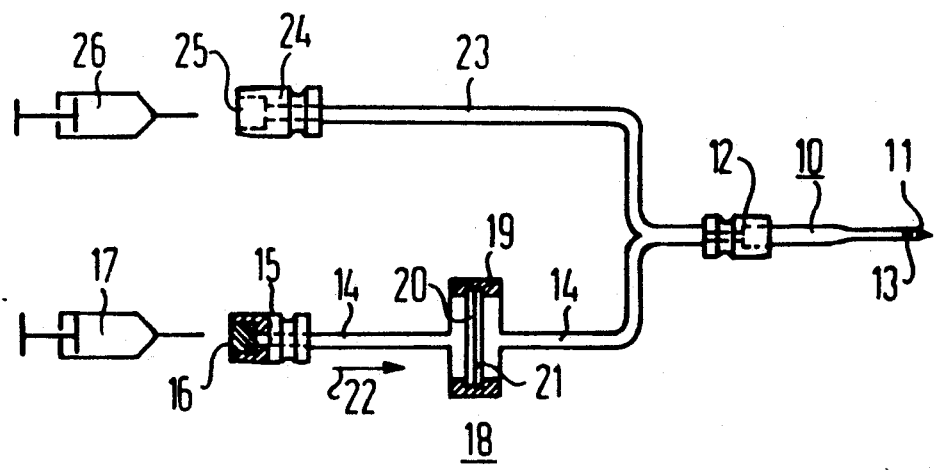
FIG. 2 is a schematic diagram of an arrangement for refilling an implanted medical dosing device of the type shown in FIG. 1 with liquid medication, constructed in accordance with the principles of the present invention.

An arrangement for replenishing the liquid medication in the reservoir 1 of the medication dosing device of FIG. 1 is shown in FIG. 2, also in simplified form. The arrangement includes a cannula 10 adapted for piercing the refilling septum 3 which has a paracentesis end in the form of a conical point 11, and an opposite end disposed in a grippable holder 12 consisting of sterilizable material, for example polycarbonate. At a distance form the point 11, referred to as the paracentesis stroke, the cannula 10 is provided with a lateral opening 13 having exterior edges which are rounded. This insures that the septum material will not be damaged or severely cut when it is pierced by the cannula 10, but is instead circularly, elastically opened by the displacement of the septum material by the cannula 10.

Among other things, the holder 12 serves to connect the cannula 10 to a flexible conduit 14, which discharges into a handle 15, and is terminated at that location by a further pierceable septum 16. The medication to be replenished can be applied through the arrangement into the medication reservoir with a refilling syringe 17 inserted through the pierceable septum 16.

A filter arrangement 18 is disposed in the path of the flexible conduit 14. The filter is preferably a two-ply membrane filter having membranes 20 and 21 secured to an annular retaining frame 19. The first membrane 20, as seen in the flowing direction 22 of the medication, consists of polypropylene fiber fleece oriented opposite to the flow direction 22, and having supporting fleece fibers. The membrane 21, disposed downstream of the membrane 20, consists of a braided weave of polypropylene. The flow-through opening has an area of approximately 1 cm$^2$, and the thickness of the first membrane 20 is selected so that it has a retention rate of greater than or equal to 5 $\mu$m, given a medication flow of 50-120 ml per minute and a maximum pressure differential of 100 mbar. Due to its type of weave, the second membrane 21 has pores which do not extend straight through the membrane 21, and which have a size of approximately 25 $\mu$m. The second membrane 21 will thus retain any fibers which may possibly separate from the first membrane 20. The filter thus achieves good particle retention, but permits a low filling pressure (approximately 10 mbar) and a short filling time (approximately 1 minute).

In the region between the filter 18 and the cannula 10, the cannula 10 is connected via a conduit branch to a further flexible conduit 23, which discharges into a further handle 24 and is terminated at that location by a further pierceable septum 25. Through the pierceable septum 25 and the flexible conduit 23, medication residues can be extracted from the medication reservoir 1 by an extraction syringe 26, before refilling takes place.

The conduits 14 and 23 consist of medication-compatible material which is resistent to compression at the negative pressures which are expected to be present in the arrangement. The conduits 14 and 23 may consist, for example, of polypropylene or polyethylene. The pierceable septa 16 and 25 preferably consist of bromobutyl rubber having a negative pressure-resistant thickness of at least 1 mm.

Emptying and refilling of the medication reservoir in the medication dosing device as shown in FIG. 1 is achieved with the skin 4 and the refilling septum 3 of the dosing device being first pierced by the cannula 10, so that access to the medication reservoir 1 is obtained. Using the extraction syringe 26 inserted into the further pierceable septum 25, the entire implanted arrangement is evacuated and the residual volume of medication is thus removed from the medication reservoir 1, causing the membrane bellows 5 to contract. The extracted medication is discarded, and the extraction procedure is repeated. Subsequently, the extraction syringe 26 is withdrawn, with the septa 16 and 25 insuring that the negative pressure in the arrangement is maintained.

For refilling the medication reservoir 1, the refilling syringe 17 is filled with fresh medication, free of air bubbles, and is inserted into the pierceable septum 16. The medication is drawn from the syringe 17 by suction due to the negative pressure prevailing in the arrangement, until a pressure equalization occurs after the medication has been completely drawn in.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for filling a reservoir for use with a source of negative pressure, said apparatus comprising:
   a cannula having a paracentesis end shaped for hermetic introduction into a reservoir to be filled with fluid, and having an opposite end;
   first and second flexible conduits in fluid communication with said opposite end of said cannula, each flexible conduit terminating in a free end;
   first and second pierceable septa respectively attached to said free ends of said first and second flexible conduits; and
   said second septum forming means for communicating said second flexible conduit and said cannula with said source of negative pressure for creating a negative pressure at said cannula for drawing fluid supplied through said first septa and said first flexible conduit into said cannula.

2. An apparatus as claimed in claim 1 further comprising:
   filter means disposed in said first flexible conduct for filtering medication supplied to said filter means through said first pierceable septum.

3. An apparatus as claimed in claim 1 wherein said first and second flexible conduits and said first and second septa consist of compression-proof material capable of withstanding said negative pressure.

4. An apparatus as claimed in claim 2 wherein said filter means is a two-ply membrane filter having a first membrane disclosed closer to said first pierceable septum and consisting of polypropylene fiber fleece oriented opposite to a medication flow direction from said first pierceable septum, and a second membrane consisting of a braided weave.

5. An apparatus as claimed in claim 4 wherein said first membrane has a retention rate of greater than or equal to 5 $\mu$m given an area of approximately 1 cm$^2$, a medication flow of 50-120 ml per minute and a maximum pressure differential of 100 mbar, and said second membrane has a pore size of 25 $\mu$m with no pores extending straight through said second membrane.

* * * * *